United States Patent
Serri et al.

(10) Patent No.: US 11,503,997 B2
(45) Date of Patent: Nov. 22, 2022

(54) METHOD AND APPARATUS FOR MEASUREMENT OF A CHARACTERISTIC OF AN OPTICAL SYSTEM

(71) Applicant: EyeQue Inc., Newark, CA (US)

(72) Inventors: John Serri, Newark, CA (US); Noam Sapiens, Newark, CA (US)

(73) Assignee: EyeQue Inc., Newark, CA (US)

( * ) Notice: Subject to any disclaimer, the term of this patent is extended or adjusted under 35 U.S.C. 154(b) by 249 days.

(21) Appl. No.: 16/809,482

(22) Filed: Mar. 4, 2020

(65) Prior Publication Data

US 2020/0196859 A1  Jun. 25, 2020

Related U.S. Application Data

(63) Continuation-in-part of application No. 16/276,302, filed on Feb. 14, 2019, now Pat. No. 10,588,507, which is a continuation-in-part of application No. 15/491,557, filed on Apr. 19, 2017, now Pat. No. 10,206,556.

(60) Provisional application No. 62/813,488, filed on Mar. 4, 2019, provisional application No. 62/409,276, filed on Oct. 17, 2016.

(51) Int. Cl.
| | |
|---|---|
| *A61B 3/103* | (2006.01) |
| *A61B 3/032* | (2006.01) |
| *A61B 3/036* | (2006.01) |
| *A61B 3/00* | (2006.01) |
| *A61B 3/04* | (2006.01) |
| *A61B 3/14* | (2006.01) |

(52) U.S. Cl.
CPC .............. *A61B 3/103* (2013.01); *A61B 3/005* (2013.01); *A61B 3/032* (2013.01); *A61B 3/036* (2013.01); *A61B 3/04* (2013.01); *A61B 3/14* (2013.01)

(58) Field of Classification Search
CPC ......... A61B 3/103; A61B 3/005; A61B 3/032; A61B 3/036; A61B 3/04; A61B 3/14
USPC .......................................................... 351/239
See application file for complete search history.

(56) References Cited

U.S. PATENT DOCUMENTS

| | | | |
|---|---|---|---|
| 2003/0151721 A1* | 8/2003 | Lai ........................ | A61B 3/103 351/212 |
| 2009/0021832 A1* | 1/2009 | Jackson ............. | G02B 27/4211 359/566 |
| 2009/0153796 A1* | 6/2009 | Rabner ................. | A61B 3/024 351/203 |

* cited by examiner

*Primary Examiner* — Mohammed A Hasan
(74) *Attorney, Agent, or Firm* — Steven A. Nielsen; www.NielsenPatents.com

(57) ABSTRACT

Disclosed embodiments may include a device, system and method for providing a low cost device that can measure refractive errors very accurately via attachment to a smart phone. A disclosed device may use ambient light or a light source in simulating the cross cylinder procedure that optometrists use by utilizing the inverse Shack-Hartman technique. The optical device may include an array of lenslets and pinholes that will force the user to effectively focus at different depths. Using an optical device, in conjunction with a smart phone, the user first changes the angle of the axis until he/she sees a cross pattern (the vertical and horizontal lines are equally spaced). The user adjusts the display, typically using the controls on the smartphone, to make the lines come together and overlap, which corresponds to bringing the view into sharp focus, thus determining the appropriate optical prescription for the user.

13 Claims, 13 Drawing Sheets
(13 of 13 Drawing Sheet(s) Filed in Color)

Example of A Coma-Free Pattern From A User's Perspective

Example of Coma-Induced Pattern From A User's Perspective

Simple Inverse Shack-Hartmann Optical Schematic - Initial Position

Simple Inverse Shack-Hartmann Optical Schematic - Single Pixel Displacement

Different Rotation Methods for Measuring Different Meridians

Rotation Around the Center of the Lines

Phone Screen

Rotation Around the Center of the Pattern

⊕ Center of Rotation

Phone Screen

Simulation Result of Comma and Crosstalk

Magnification Stage

Integrated Optical System

Integrated Optical System of the Second Embodiment

METHOD AND APPARATUS FOR MEASUREMENT OF A CHARACTERISTIC OF AN OPTICAL SYSTEM

RELATED PATENT APPLICATION AND INCORPORATION BY REFERENCE

This is a Continuation in Part (CIP) utility application based upon and claiming priority from U.S. patent application Ser. No. 16/276,302 filed on Feb. 14, 2019 which is a CIP of U.S. patent application Ser. No. 15/491,557 filed on Apr. 19, 2017 and now U.S. Pat. No. 10,206,566 issued on Feb. 19, 2019, which claims priority from provisional patent application Ser. No. 62/409,276 filed on Oct. 17, 2016. This application also claims the benefit and priority of provisional patent application 62/813,488 filed on Mar. 4, 2019. The related applications are incorporated herein by reference and made a part of this application. If any conflict arises between the disclosure of the invention in this utility application and that in the related applications, the disclosure in this utility application shall govern. Moreover, the inventor(s) incorporate herein by reference any and all patents, patent applications, and other documents hard copy or electronic, cited or referred to in this application.

COPYRIGHT AND TRADEMARK NOTICE

This application includes material which is subject or may be subject to copyright and/or trademark protection. The copyright and trademark owner(s) has no objection to the facsimile reproduction by any of the patent disclosure, as it appears in the Patent and Trademark Office files or records, but otherwise reserves all copyright and trademark rights whatsoever.

BACKGROUND OF THE INVENTION

(1) Field of the Invention

The invention generally relates to optometers and the assessment of refractive disorders of the human eye. More particularly, the invention relates to the use of hand held consumer devices used for self-refraction.

(2) Background

Disclosed embodiments may measure the refractive properties of an optical system by simulating the cross-cylinder procedure that optometrists use in a clinical setting. An optical system as defined herein can include, but is not limited to, the human eye and mechanical systems wherein refractive measurement can determine a refractive error. Disclosed embodiments may comprise extensions and improvements upon the methods described in published patent application US 2013/0027668 A1 by Pamplona et al which discloses the creation of a low cost device that can measure refractive errors using a smart phone as a light source. However, the method and device described in the prior art is limited to optical systems consisting of a single multi-lens array or a pin hole array, which is neither as accurate and easy to use nor as economical as the embodiments described herein. Thus, there is a need in the art for new systems and methods using ubiquitous smart phones which can measure the refractive properties of an optical system.

BRIEF SUMMARY OF THE INVENTION

Disclosed systems and methods include methods that simulate or replicate an optometrist's cross-cylinder examination that utilizes the inverse Shack-Hartmann technique. Disclosed systems and methods include various improvements, such as accuracy and usability of the inverse Shack-Hartmann technique. The optical input of a disclosed device can originate from a smart phone, personal electronic device or other optical system, wherein the user will see two parallel lines looking through the other end of the device (e.g. one green and one red) separated by a specific distance d (see FIG. 1). The lines may be generated from the screen of a smartphone. The high resolution afforded in today's smart phones (e.g. iPhone 6 has a 326 dpi screen resolution that corresponds to a pixel spacing of about 78 microns) allows for high resolution measurements of the optical displacement or error if referencing an entity such as a focal plane or human retina. After the light passes through the optical system, at the imaging plane two lines are formed, (see FIGS. 1 and 2) and in a particular embodiment, two lines with "tails", as seen in FIG. 3, due to the intended coma in the described system. The coma, or comatic aberration, in an optical system referring to an aberration inherent to certain optical designs or due to imperfection in the lens or other components that results in off-axis point sources such as pixels forming a line are appearing distorted, appearing to have a tail (coma) like a comet. Specifically, coma may be defined as a variation in magnification over the entrance pupil. In refractive or diffractive optical systems, especially those imaging a wide spectral range, coma can be a function of wavelength, in which case it is a form of chromatic aberration.

If the imaging system or the eye being tested has a refractive error, the lines will be out of focus and separated, as shown in FIG. 4. The imaging plane may be the eye retina or the sensor of a CCD camera. By changing the distance d (see FIG. 1) between the two lines on the smart phone until the user perceives a zero or near zero distance (see "aligned lines" in FIGS. 3, 4), a refraction error may be assessed.

The distance of the lenslets from the smartphone's screen is D which is equal to the focal length of each lenslet. Thus, after the incident light passes through the lenslets, it becomes collimated and focuses on the focal plane of the lens of the tested lens. If there is a refractive error, the red and green lines are separated on the imaging plane as shown in FIG. 4A. If the lines are moved on the screen by changing the distance d, the position of the two lines on the imaging plane will also change. When the two lines are overlapping on the imaging plane the refractive error can be assessed by the amount of change for distance d.

BRIEF DESCRIPTION OF THE DRAWINGS

The patent or application file contains a least one drawing executed in color. Copies of this patent or patent application publication with color drawing(s) will be provided by the Office upon request and payment of the necessary fee.

REFERENCE NUMERALS IN THE DRAWINGS

Figure 1:
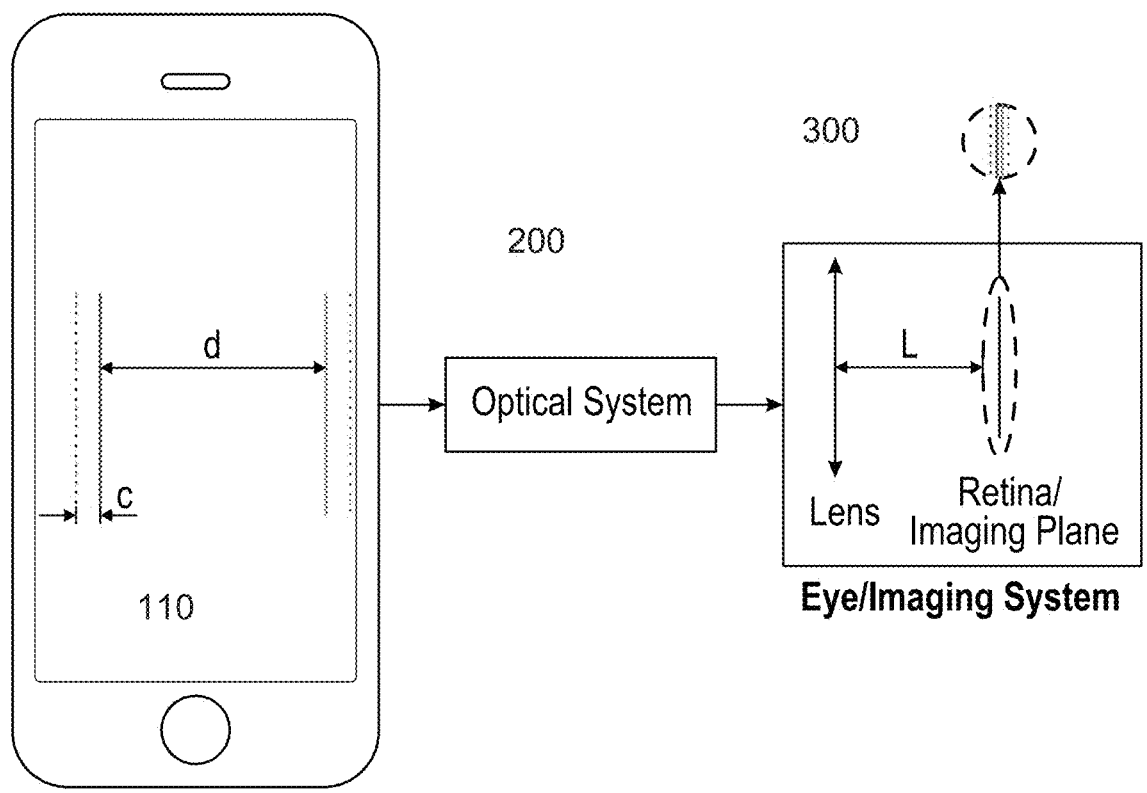
FIG. 1 depicts a schematic diagram of an overall configuration of a disclosed system with the light source being a smart phone screen, and depicts the effect of moving the lines by one pixel with size c.

These and other aspects of the present invention will become apparent upon reading the following detailed description in conjunction with the associated drawings.

L1 de-magnifying lens
L2 a color lens or second lens
L3 a color lens or another second lens
100 smart phone
110 screen of smart phone
112 display
200 optical system
210 focal plane
220 imaging plane
230 convex lens
240 concave lens
300 eye/imaging system
400 optical axis
500 lenslets
600 complex lens

DETAILED DESCRIPTION OF EMBODIMENTS OF THE INVENTION

The following detailed description is directed to certain specific embodiments of the invention. However, the invention can be embodied in many different ways as defined and covered by the claims and their equivalents. In this description, reference is made to the drawings wherein like parts are designated with like numerals throughout.

Unless otherwise noted in this specification or in the claims, all of the terms used in the specification and the claims will have the meanings normally ascribed to these terms by workers in the art.

Unless the context clearly requires otherwise, throughout the description and the claims, the words "comprise," "comprising" and the like are to be construed in an inclusive sense as opposed to an exclusive or exhaustive sense; that is to say, in a sense of "including, but not limited to." Words using the singular or plural number also include the plural or singular number, respectively. Additionally, the words "herein," "above," "below," and words of similar import, when used in this application, shall refer to this application as a whole and not to any particular portions of this application.

Disclosed embodiments may use the inverse Shack-Hartmann method and a procedure that emulates the cross-cylinder procedure that many optometrists use in order to determine refractive errors with high accuracy.

A method used by an optometrist to accurately measure the refractive error of a patient includes: initially the optometrist has a rough estimation of the patient's refractive error and using a cross cylinder or equivalently, a Jackson's cross cylinder, the optometrist can accurately determine the axis and the amplitude of the astigmatism. Using this method, the optometrist first estimates the prescription using another refractive method such as an autorefractor or retinoscopy. Then the optometrist uses this prescription as a base line and adds a pure cylindrical lens with zero spherical equivalent and cylindrical power 2 C. Thus, the power of the lens on one axis is +C and on the other axis which is perpendicular to the first one is −C. The optometrist initially aligns the axis of the estimation of the prescription with the meridian that has 0 power. Then the optometrists flips the lens, changing the polarity of the lens at each meridian or equivalently changes the axis of the cylinder by 90 degrees. If the initial axis is correct the patient will not notice any difference, the blur would be the same. If the patient notices a difference, the patient chooses the position (axis) that sees the best image. Then, the optometrist rotates the correcting lens 5 degrees towards the axis that gave the best quality image. This process is repeated until the patient cannot notice any difference. This is how the axis is determined with high accuracy. Then the optometrist fine tunes the power of astigmatism. The optometrist, using the new axis for setting up the lens kit, uses the same cross-cylinder lens as before but now the axis of astigmatism is parallel with one of the principal meridians of the cross cylinder. The optometrist then flips the cross-cylinder lens and changes the power of corrective cylinder according to patient's directions (which position has the least blur) until the patient cannot notice any difference, perceiving the same blur for both positions of the cross-cylinder.

In a disclosed embodiment, using a simple inverse Shack-Hartmann implementation to measure the refractive error, the user observes two lines on a screen such as the screen of a smartphone through an optical system as shown in FIG. 1. Then looking through the refractive device the user changes the distance between the two lines on the screen until the user sees the two lines overlapped. Then the user moves or adjusts the device to move on to the next meridian, wherein two more lines are presented to the user. This process emulates the addition of a corrective lens in front of the eye and/or camera until a sharp image is formed.

The optical system, according to regular inverse Shack-Hartmann method, can be a micro-lens array and/or a pinhole array. The distance of the optical system from the phone screen is defined as D.

Figure 2:
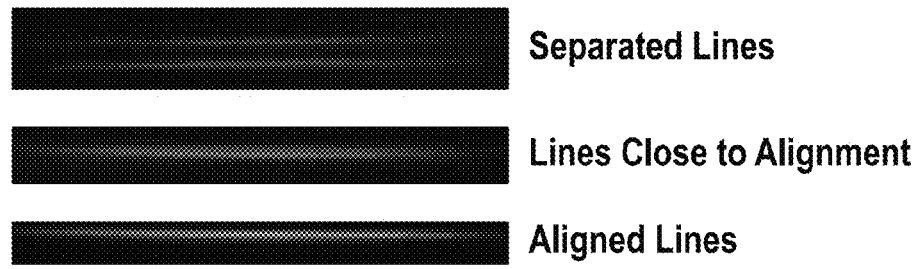
FIG. 2 depicts what a user might see as they operate a disclosed device, using comma-free lines.

FIG. 2 depicts what a user might see as they operate a disclosed device, using a screen pattern of two lines, one red and one green. The operation or function of bringing lines together as seen through a disclosed device will be referred to or defined as "alignment", and at the end of this process when the lines appeared together and/or overlapping will be referred to or defined as "aligned". The minimum distance that the user can move the lines is limited by the phone's resolution, namely the pixel distance c, and the distance between the screen and the optical system D. When the user changes the distance on the phone it changes the angle of the incident light to the imaging system (see FIG. 4). The minimum change in the incident angle to the imaging system $\theta_{min}$ can be calculated from the following formula:

$$\theta_{min} = \tan^{-1} \frac{c}{D}$$

Figure 4A:
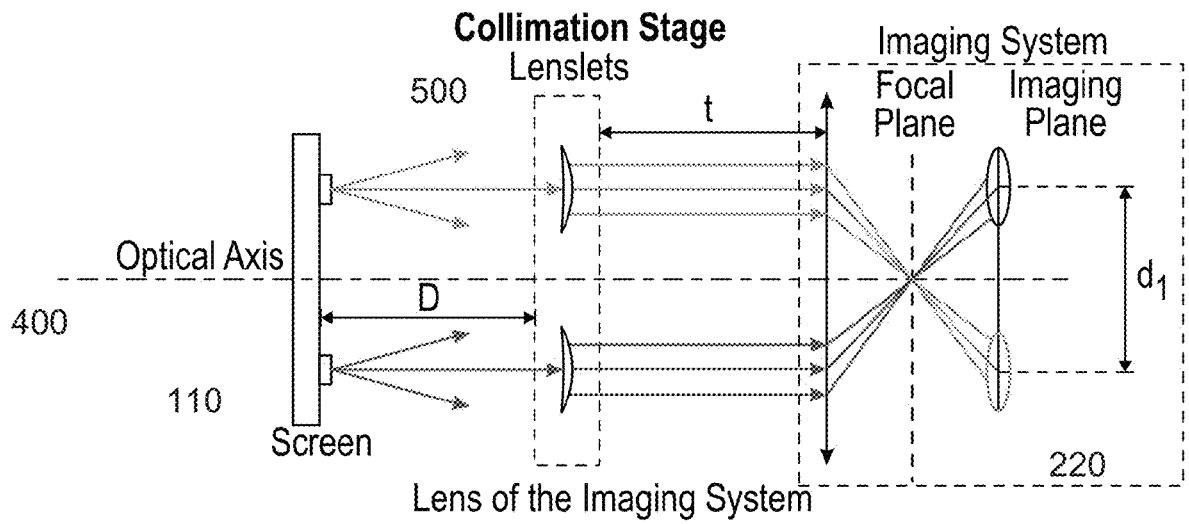
FIG. 4A depicts an implementation of the Inverse Shack Hartmann technique in an initial position.
Figure 4B:
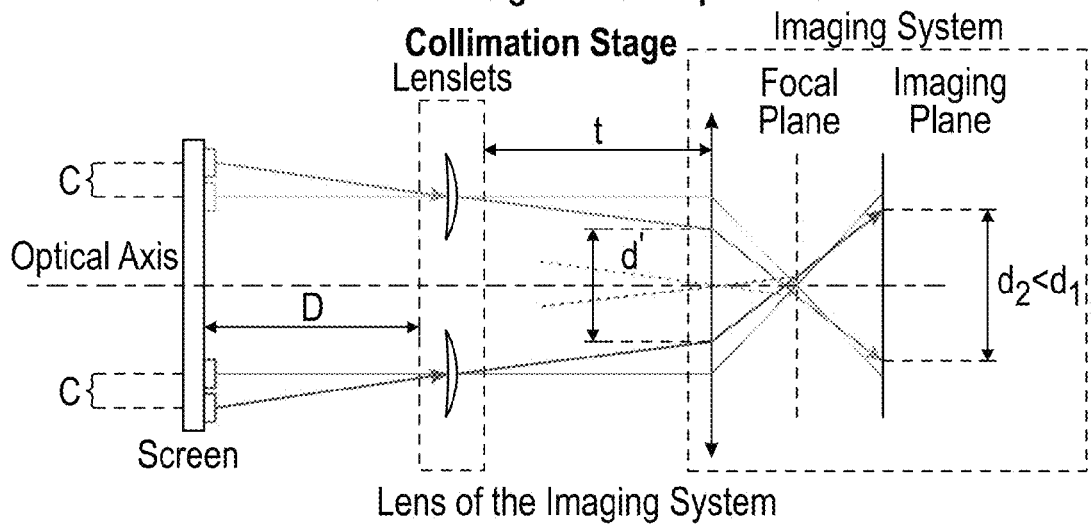
FIG. 4B depicts an implementation of the Inverse Shack Hartmann technique wherein the pixels have been moved by one pixel

By knowing the distance d of the two lines on the phone screen, and the distance D the incident angle can be calculated. From the incident angle θ the power of the refractive error P can be calculated in diopters ($m^{-1}$). Thus the amount of correction P that is needed can be calculated using the following equation:

$$P = \frac{2\tan\theta}{d'}$$

where d' is the distance of the two beams on the lens of the imaging system or the size of the exit pupil as shown in FIG. 4B.

Thus the resolution of the refractive error that can be detected in a system as in FIG. 4B is:

$$P_{min} = \frac{2c}{Dd'} = \frac{2c}{fd'} = \frac{2c}{f(d - 2tc/f)}$$

This formula assumes that the lines are overlapping exactly in the center of the imaging plane. As an example, if the pixel distance c is 0.78 µm the size of the entrance pupil of the imaging system d' 1.5 mm and the focal length 10 cm the minimum refractive error that can be detected is about 1 diopter.

Figure 5A:
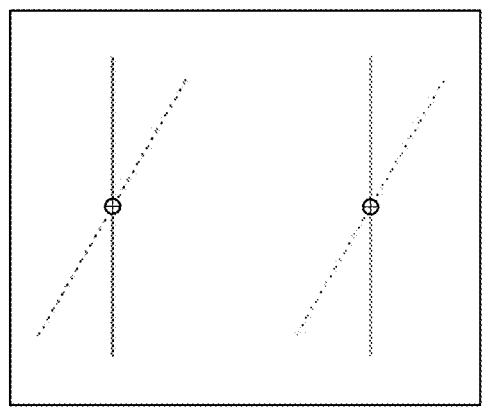
FIG. 5A depicts a display with the pattern used as an input to the optical system using a rotation of the lines around their center to measure different meridians.
Figure 5B:
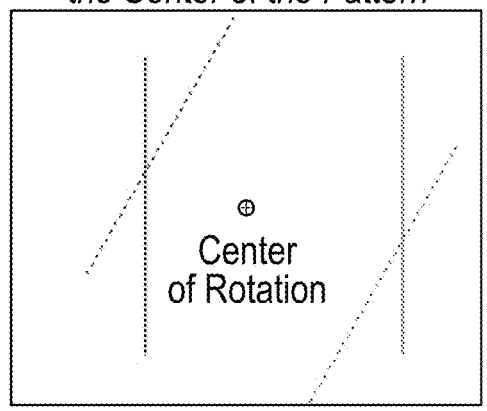
FIG. 5B depicts a display with the pattern used as an input to the optical system using a rotation of the lines around the center of the screen to measure different meridians.

The described measurement takes place one meridian at a time by virtue of using one pair of parallel lines. In order to measure different meridians through the camera or human eye, the angle of the parallel lines must change with respect to the orientation of the human eye. At different meridians the space between the lines on the phone screen needed to reach alignment can be different because the power at each meridian changes due to astigmatism. The angle of the lines, and consequently the meridian that is being tested, can be changed either by rotating the lines around the center of each line or around the center of the pattern (see FIGS. 5A, 5B). In order to have representative points across all the meridians at least one rotation around the center of the pattern is needed, see FIG. 5B, otherwise the meridian that corresponds to the initial meridian plus 90 degrees cannot be measured. When the lines are rotating around the center of the pattern the optical elements should also follow the rotation of the lines. This can be done either by rotating the optical elements to match the rotation of the pattern or by rotating the whole display (phone). One other way is by using more optical elements (micro-lenses, pinholes etc.). In this case the pattern is rotated on the phone and uses different lenslets or pinholes to collimate the light. In this case there is crosstalk which can confuse the user.

With the technique described herein, disclosed embodiments using the inverse Shack-Hartmann technique, simulates the cross-cylinder procedure used by optometrists. The disclosed embodiments are made possible, in part, by the several disclosed improvements on the inverse Shack-Hartmann method that are disclosed herein. A disclosed optical device may include an array of lenslets and/or pinholes used with a light source as in the Shack-Hartmann technique discussed above. Using this disclosed optical device, in conjunction with a smart phone the cross-cylinder procedure described above can be emulated.

Figure 9:
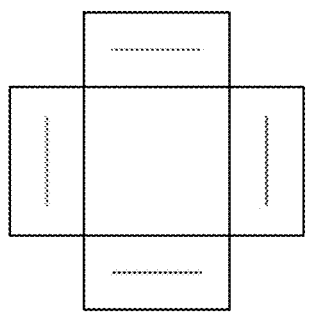
FIG. 9 depicts the usage of an inverse Shack-Hartmann method for validating a prescription and for the illustration of results
Figure 9:
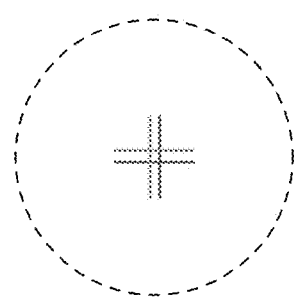
Figure 9:
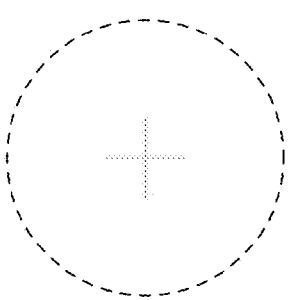

In one disclosed embodiment, the screen of the smartphone displays simultaneously four lines, two pairs of parallel lines, as shown in FIG. 9. The two parallel pairs are perpendicular to each other and the separation of the lines at each pair is always the same. When the user looks through the optical device the screen of a smartphone he sees two pairs of parallel lines, in total four lines. The distance of the lines within a pair that the user perceives depends upon the refractive power of his eye at the meridian perpendicular to the lines and the distance of the lines on the phone. If the user has an astigmatic error the distance of the lines at each pair would be different unless the meridians that are being measured differ by 45 degrees from the axis of the astigmatic error (the two meridians that are being measured are the green circles in FIG. 12). When the separation of the lines at each pair is different the user rotates the pattern on the screen and hence the angle of the meridians that are being measured is changing, until the user sees two displaced crosses, FIG. 9 (the lines at each pair are equally spaced). The user adjusts the distance between the lines at each pair of lines, typically using the controls on the smartphone, to make the lines come together and overlap, which effectively corresponds to bringing the view into sharp focus.

Figure 12A:
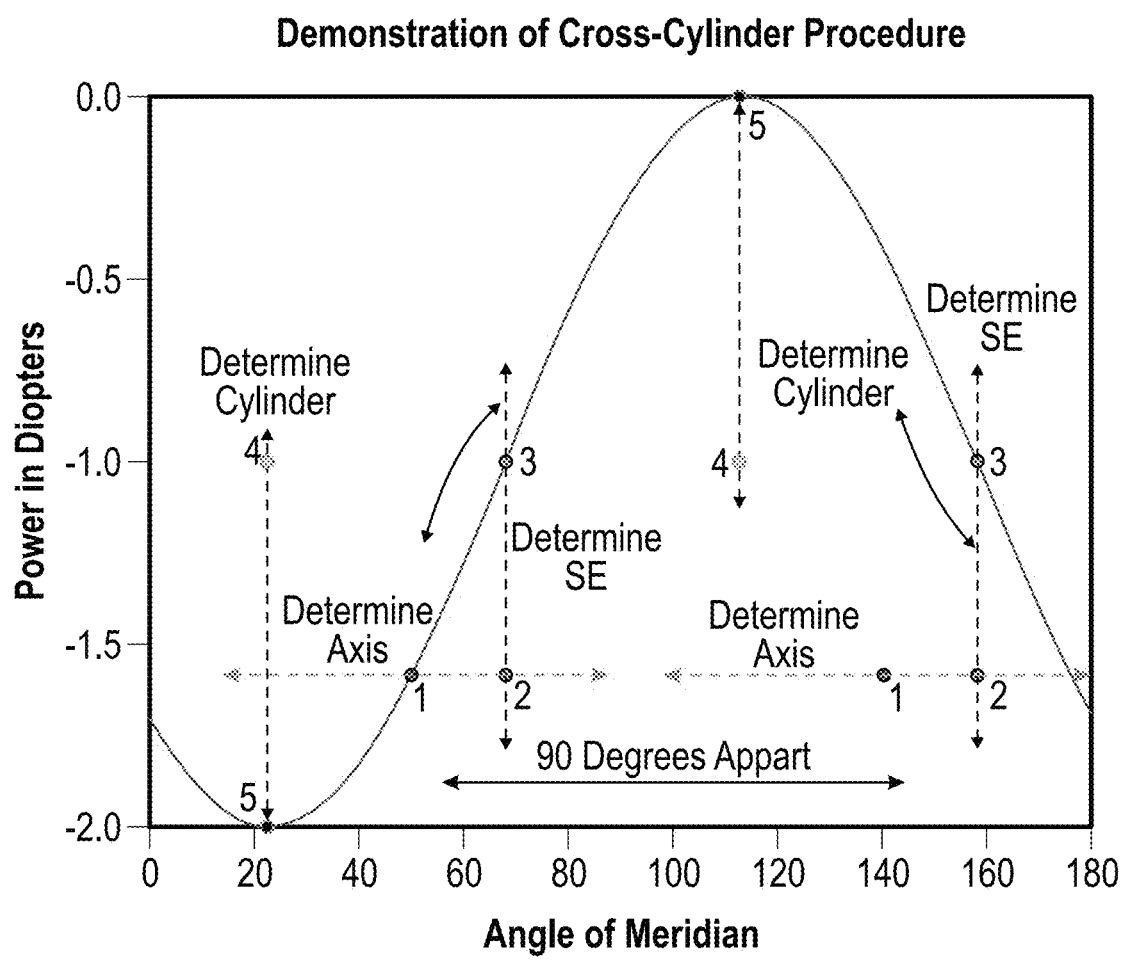
FIG. 12A depicts graphic representation of the use of the inverse Shack-Hartmann technique wherein a disclosed embodiment can simulate a cross cylinder procedure for accurately estimating the refraction error and lens properties.
Figure 12B:
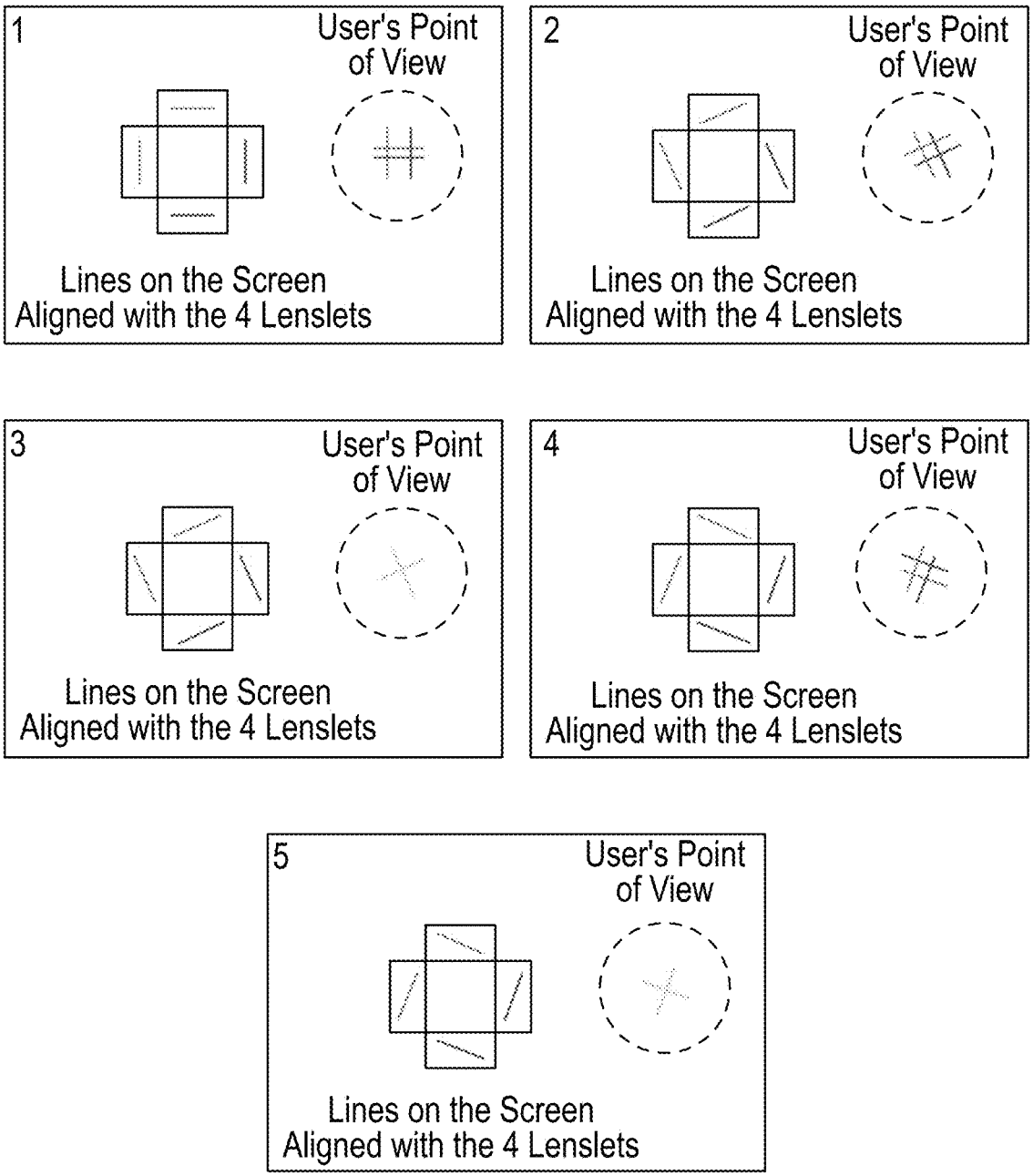
FIG. 12B depicts graphic representation of what the user perceives and the state on the screen of the phone at the five points illustrated in FIG. 12A.
Figure 13:
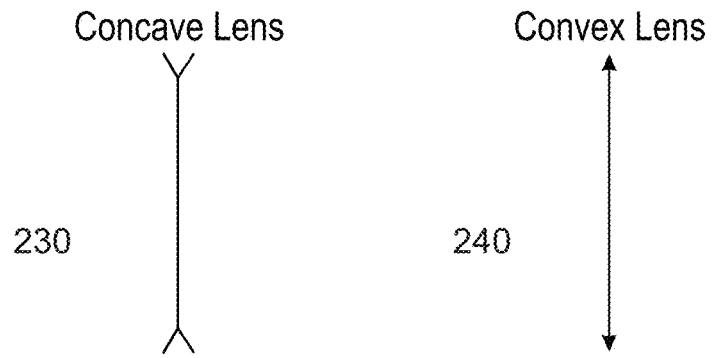
FIG. 13 depicts a drawing convention for concave and convex lenses as used in the drawings.

This procedure is graphically shown in FIG. 12A along with what the user observes at each step. The blue line represents the power of the refractive error (y-axis) at each meridian (x-axis). At this particular example a refractive error of 0 spherical −2 cylindrical with axis of 25 was used. When the user rotates the pattern on the phone's screen, it effectively moves horizontally the red circles in FIG. 12A, which correspond to the meridians that are being test. As seen in FIG. 12B on the screen the lines are rotating around their center but the user sees the distance of the lines changing. The red squares are always separated by 90 degrees. When the two meridians under test have the same power (they are at the same angle as the green circles on FIG. 12A) the axis can be defined. The user knows that the two meridians under measurement have the same power when he or she sees the lines at each pair equally spaced, FIG. 12B. It is worth mentioning that during this process the lines at each pair are separated by the same amount. The meridians that are being measured at this point ±45 degrees from the axis, and hence the axis is determined.

Then the user changes the power of the spherical equivalent until the lines at each pair are overlapping and the user sees the lines at each pair are overlapping and if at each pair there is one red and one green line, the user will see a yellow cross. The change of the spherical equivalent changes the separation distance at each pair simultaneously. When the lines are overlapping, the spherical equivalent can be inferred by knowing the distance of the lines on the screen. If the user doesn't see a cross, this step and the previous step can be iterated until the user sees a yellow cross (where the red and green lines overlap). At the end of this measurement the axis of astigmatism and the spherical equivalent has been determined.

The next step is to determine the power at the axis of the astigmatic error, namely the cylinder. At the beginning of this stage the app or the user rotates the pattern on the phone by 45 degrees compared the rotation at the previous step so one of the pairs is parallel to the axis of astigmatism and the second pair to be perpendicular to the axis of astigmatism. Now the user changes the power of the cylinder by changing the separation of the lines at each pair until a yellow cross is formed as before, or equivalently the gray circles coincides with the black circles in FIG. 12A. From this last measurement, the power of the cylinder is determined.

In sum, the following steps are sometimes used to measure the refractive error of the user using this disclosed:

1. The user looks through the device viewing the smartphone's screen seeing the four lines on the phone screen, FIG. 9

2. Rotate the cross pattern on the device until the distance between the two lines at each pair (red and green) is the same;

3. Change the spherical equivalent power by changing the distance between the lines until the user sees a yellow cross or as close as possible;

4. Iterate steps 2 and 3 until the user sees a yellow cross in the middle of the field of view;

5. Rotate the pattern by 45 degrees in order to measure the power of the meridians that have the minimum and maximum power;

6. Change the cylindrical power, the amplitude of the sinusoidal in FIG. 12A until the user sees a yellow cross.

An advantage of this disclosed method is that the measurement is taking place at two meridians, 90 degrees apart, simultaneously. Thus the eye is at the same state when the measurement is taking place at both meridians. Hence, a more accurate measurement of the refractive errors is expected or at least a measurement that will yield better visual acuity results, since the estimation of the cylinder and the axis will have less noise. This is true because this method avoids errors in astigmatism due to fluctuation of the accommodation (e.g. dark focus variation, instrument myopia, etc.) since the measurements needed to estimate the amplitude and the axis of the astigmatism take place at the same time.

Figure 3:
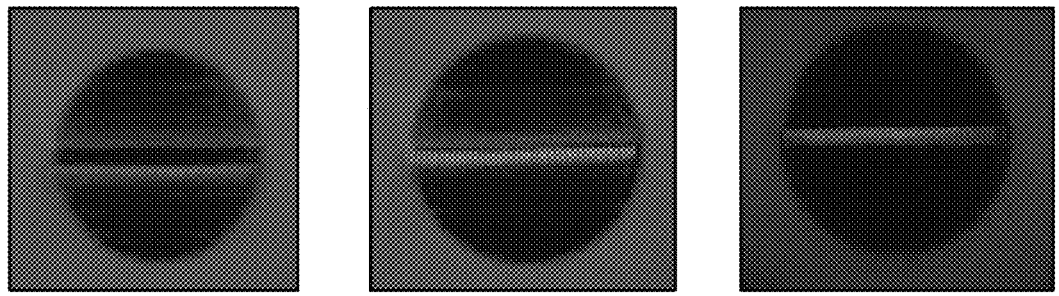
FIG. 3 depicts what a user might see as they operate a disclosed device, using non-uniformly broaden fat lines due to intentional comma in the optical system. The intentional coma helps the user see the pattern and facilitates the user's alignment of the lines.
Figure 6:
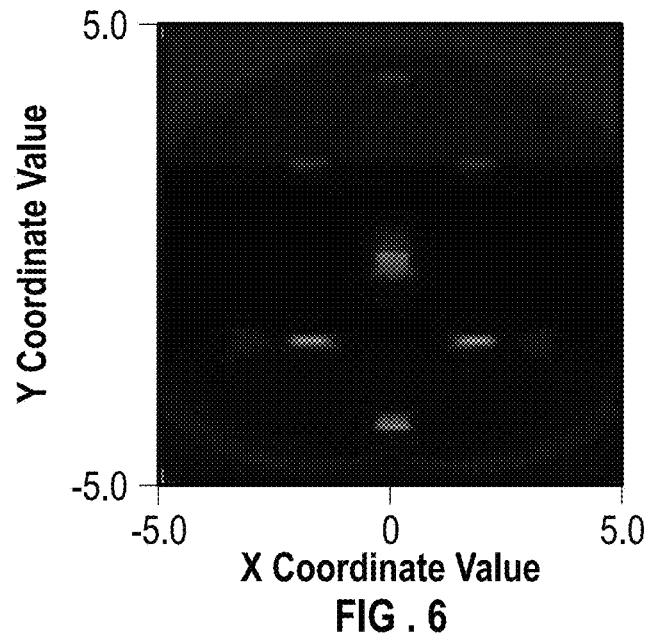
FIG. 6 depicts simulated crosstalk at the imaging plane in the inverse Shack-Hartmann technique using a complex lens as shown in FIG. 8.

To realize this cross-cylinder method, the inverse Shack-Hartmann device as shown in FIGS. 4A and 4B and described above needs some improvements as compared to the current state of the art. First, the device should be capable of handling multiple meridians at the same time. Thus at least two pairs of lenslets are needed (in total four lenslets). In this case light that was supposed to pass through a specific lenslet instead passes through another lenslet and confuses the user by creating multiple images. FIG. 6 shows this effect, which from now on we refer to as crosstalk. One way to reduce the crosstalk is to increase the distance between the two lenslets, FIG. 8, or include a baffle between the two lenslets. This way the resolution is increased (larger d'), but the exit pupil becomes larger too. In the case of the human eye, this reduces the field of view making the alignment very sensitive, as the human pupil is typically 3 to 6 mm in our conditions (1.5 mm in a very bright environment and 8 mm in an environment with very little light). Also, the resolution of the device can be improved by 2 times by allowing the overlapping to be around the center and not exactly at the center by moving one row of pixels at the time. This resembles more the reality since the lines can overlap in the center of the imaging plane only when the resolution of the device match exactly the refractive error of the user. Finally, we intentionally induced comma in our system to aid the user with the decision making. In this case the two lines are aligned when they slightly touch at the imaging plane—the user cannot see a black line between the green and red line and/or the two lines are slightly touch and a slight yellow line is formed (red and green lines are overlapped) FIG. 3.

Thus, for an ideal device high resolution is needed with a small exit pupil/large field of view, low crosstalk and an easy way for the user to make a decision when the lines are aligned, when using a subjective test method.

Definition of the Subsystems

To resolve the aforementioned issues, the following subsystems may be used:

A demagnification subsystem which comprises a single concave lens. This stage improves the resolution substantially, FIG. 7;

four lenses, 2 mm thick, 6 mm apart (center from center) to decrease crosstalk (less light that intended for one lens passes through the second lens and the image that is created is relatively far away) and defocus issues (small aperture 2 mm thick). An extra shutter in form of slits can be used in the lenses in order to further improve the usability in optical systems with higher refractive errors. These dimensions are provided as an example, however the invention is not limited to these parameters;

Magnification stage to reduce the exit pupil and improve the field of view, to further reduce crosstalk and induce comma to improve user experience.

Finally a shutter in form of a slit can be used just before the lens of the optical system under test in order to increase the depth of field. This way the blur observed by people with high refractive errors is minimized due to the small aperture in one direction and at the same time the light is attenuated much less compared to a pinhole.

Figure 7:
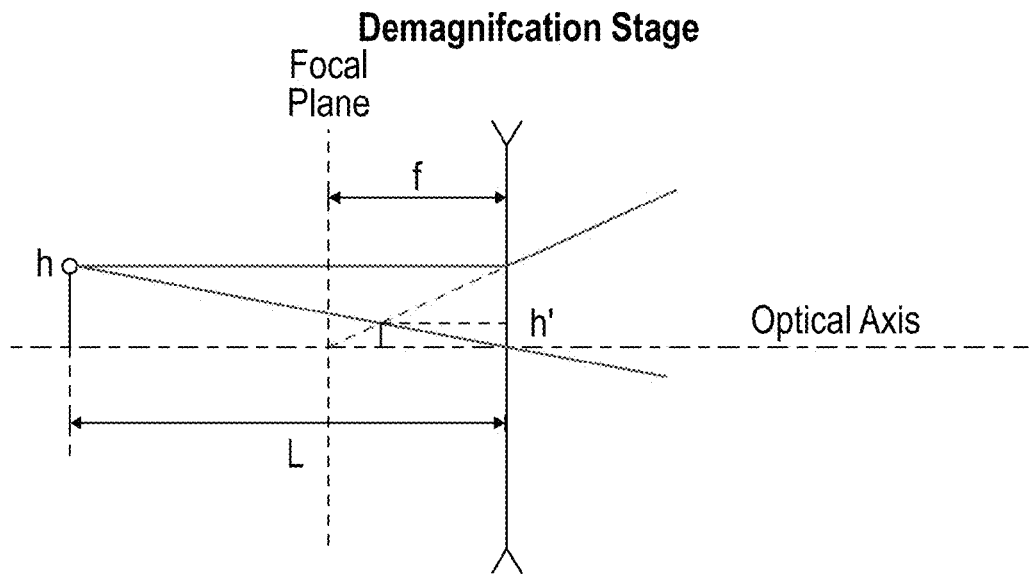
FIG. 7 depicts a demagnification stage

FIG. 7 shows the demagnification concept, which increases the effective resolution of the mobile screen. To improve the resolution, a subsystem is introduced that comprised of one concave lens. The concave lens creates a new virtual image that is smaller than the original image. If the concave lens with focal length f from the image is L then a change h in the distance from the optical axis converts into a distance h', and hence the effective pixel density is increased. The demagnification factor DM=h/h', the amount the linear pixel density is increased, is given by:

$$DM = \frac{h}{h'} = 1 + \frac{L}{f}$$

Thus by either increasing the distance from the screen or by decreasing the focal length of the lens, the demagnification factor can be increased. This can increase the effective resolution and it can have other applications not limited to this device, e.g. it can be used to increase the resolution for VR headsets. The virtual image is formed in distance L/DM behind the concave lens (towards the screen). This has an effect of increasing the linear pixel density by a factor of DM, or equivalently to decrease the minimum pixel distance by a factor of DM.

Figure 8:
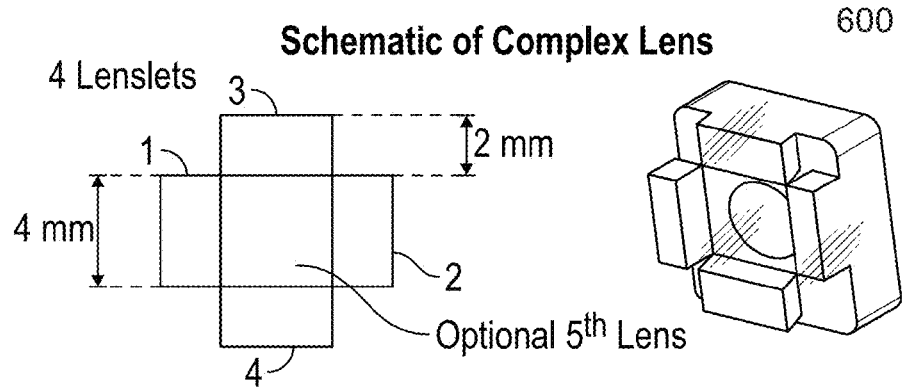
FIG. 8 depicts a lens array where an optional lens can be added and wherein the lens array may enable the use of other information, instructions, and patterns

FIG. 8 shows a lens array where an optional lens can be added that allows transmission of other information, instructions, and patterns. In this setup four lenslets are used to avoid rotation/crosstalk/defocus (four lenslets at a relatively far distance) with a fifth optional lenslet in the center of the array for allowing other optical images to be presented to the user. Other optical images can be used for controlling accommodation, or sending the user visual information and/or instructions. The four lenslets may be 2×4 mm in order to act as a small shutter and reduce the crosstalk. Light intended to go through one lens is poorly coupled to the lenses that are oriented perpendicular to the initial lens. The lenslets are used in pairs as described in the beginning of this document (lenses 1, 2 and 3, 4, FIG. 8), namely to create two collimated beams. The crosstalk is reduced because light that was directed through one 1 and 2 is poorly coupled to lenses 3 and 4 because of their shapes and vice versa. The lenslets are 6 mm apart to reduce crosstalk.

FIG. 9 shows the usage of lenses and the checking of results. To check the validity of a test result, namely if the system estimated correctly the refractive properties of the user's eyes or the device under test all four lenslets can be used simultaneously, as in the cross-cylinder method. The distance of the lines on the screen is set based on the result and the meridian under measurement. If the result is correct, the user will see a cross. For example, if the result shows a cylinder at 8 degrees and we want to check the cylinder one pair of lenses is set to measure at 8 degrees and the second pair at θ+90 modulo 180 degrees.

If measurement of the spherical equivalent is desired, a measurement at θ+45 modulo 180 degrees and at θ−45 modulo 180 degrees can be taken. At those two meridians if the estimation of the refractive error is correct the power of lens under test should be equal to spherical equivalent. If the user sees 4 lines, then the test result is incorrect (in FIG. 9 indicates wrong result). If the user sees a cross the result is valid (indicated in FIG. 9 as correct result). This way, experimental validation of the result can be produced by simultaneously measuring two meridians.

Using four lenslets relatively far away from each other with an optional 5$^{th}$ lens, crosstalk is reduced as well as any mechanical rotation is avoided, while any meridian lends itself to measurement. At the same time, the fifth lens can be used to provide the necessary stimuli in order to control the user's accommodation and project to him other useful information. The downside is that the exit pupil is pretty large and the field of view small. This issue will be addressed by the next subsystem.

Figure 10:
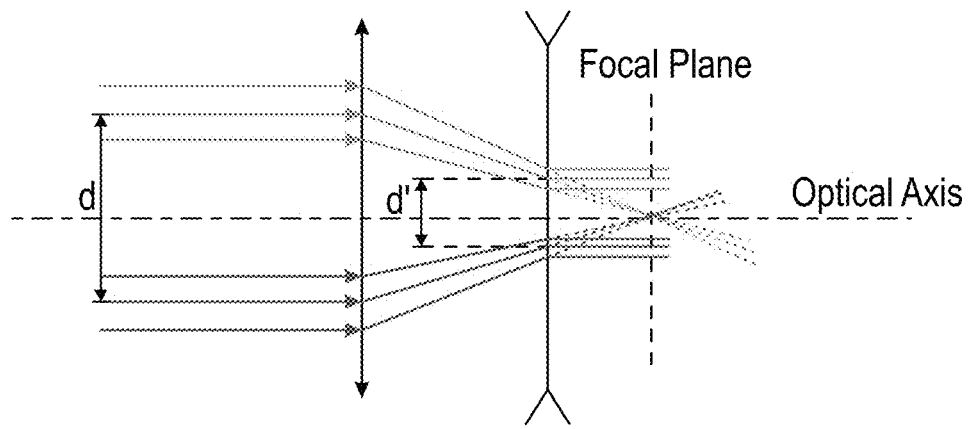
FIG. 10 depicts exit pupil reduction system in order to make the exit pupil smaller than the entrance pupil of the imaging system.

FIG. 10 shows exit pupil reduction, crosstalk reduction, and coma inducer optical system. The induced coma helps to improve usability. This subsystem has three objectives. The main objective is to reduce the exit pupil and hence to increase the field of view. Second, the crosstalk that the user perceives is further reduced because the crosstalk image is outside of user's field of view. Finally, this setup induces coma, making the lines easier to see and align (the fat line effect shown in FIG. 2).

This setup or disclosed configuration comprises a convex lens with focal length $f_1$ and a concave lens with focal length $f_2$. The two lenses share the same focal plane. The input in this system is the output of the lenslets array thus it is two collimated beams. In order to make it easy to analyze this subsystem, it shall be assumed that the two beams are parallel to the optical axis. The convex lens focuses the two parallel beams. This brings the two beams closer, and hence reduce the exit pupil. Before they reach the focus the concave lens intervenes and the two beams become parallel again, but now are much closer. The amount of the reduction of the exit pupil (d/d') equals to the ratio of the focal lengths of the two lenses ($f_1/f_2$). This has as an effect of decreasing crosstalk (the concave lens acts as a beam expander, and increases the angular separation between the main beams and the beams due to crosstalk). A second positive side-effect of this system is the coma induction. Because the edge of a spherical lens is used and is converted, an induced coma to the collimated beams is created. This results in a sharp line with a faded tail as shown in FIG. 3. This makes the alignment process more objective and the lines easier to find. Ideally, the user will place the two lines very close in order to see a slight yellow line and no gap (see FIG. 3). The downside of this system is that the resolution is significantly reduced. Two phenomena result in the reduction of the resolution: (1) the distance of the parallel beam is reduced which directly affects the resolution; and (2) for the same pixel movement there is a larger change in the incident angle to the eye which results in lower resolution.

Figure 11:
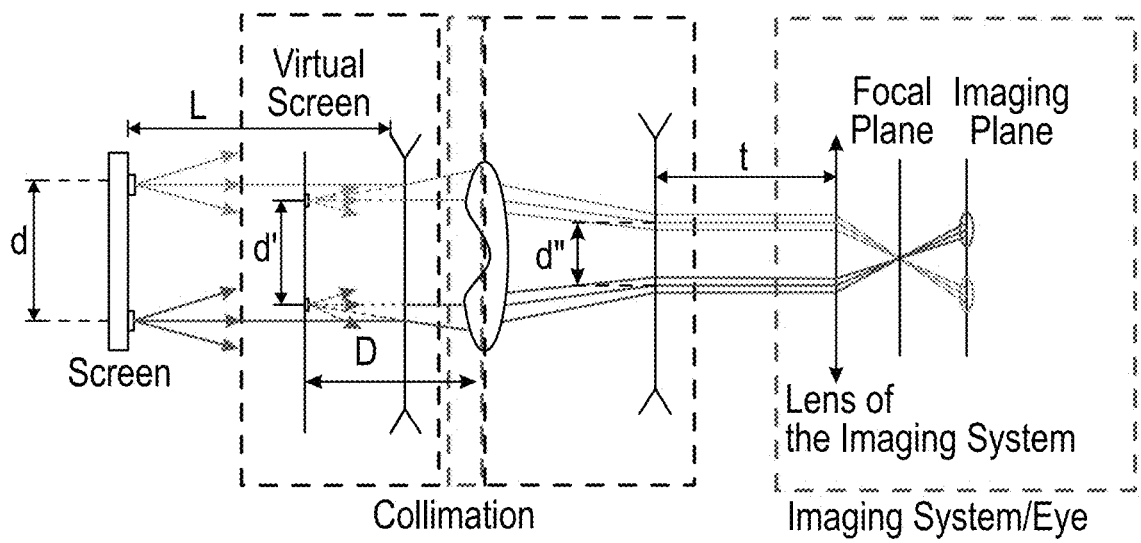
FIG. 11 depicts an overall disclosed embodiment, based upon the content of FIGS. 4, 7, 8 and 10.

FIG. 11 shows an overall disclosed system, including a description of the overall system and the optical parts. The previous subsystems, FIGS. 7, 8, 10 are realized into one complete optical system which may comprise:

A concave lens to reduce the minimum refractive error;

A lens array that collimates the light from the virtual image that is created using the concave lens, together with the convex lens of the third subsystem. This custom/complex optical element increases the transmission by approximately 8.6% and reduces the manufacturing cost significantly compared of using separate optical elements; and a second concave lens to prepare the light for the imaging system.

Thus the light from the phone display screen first passes through the first concave lens in order to increase the effective resolution. Then through a convex lenslet that is off-axis to the whole system to collimate the light parallel then to another convex lens, followed by a concave lens to reduce the exit pupil and reduce crosstalk. In order to have a calibrated measurement, the device should have an initial calibration. This can be done using a camera focused at infinity (emulates an emmetropic eye). Then an artificially induced error is created by adding a prescription lens from a trial lens-kit in front of the camera. Afterwards, the lines are moved until they touch and the amount of displacement is logged with the induced refractive error. This way, the refractive error can be determined by knowing the displacement.

Figure 14:
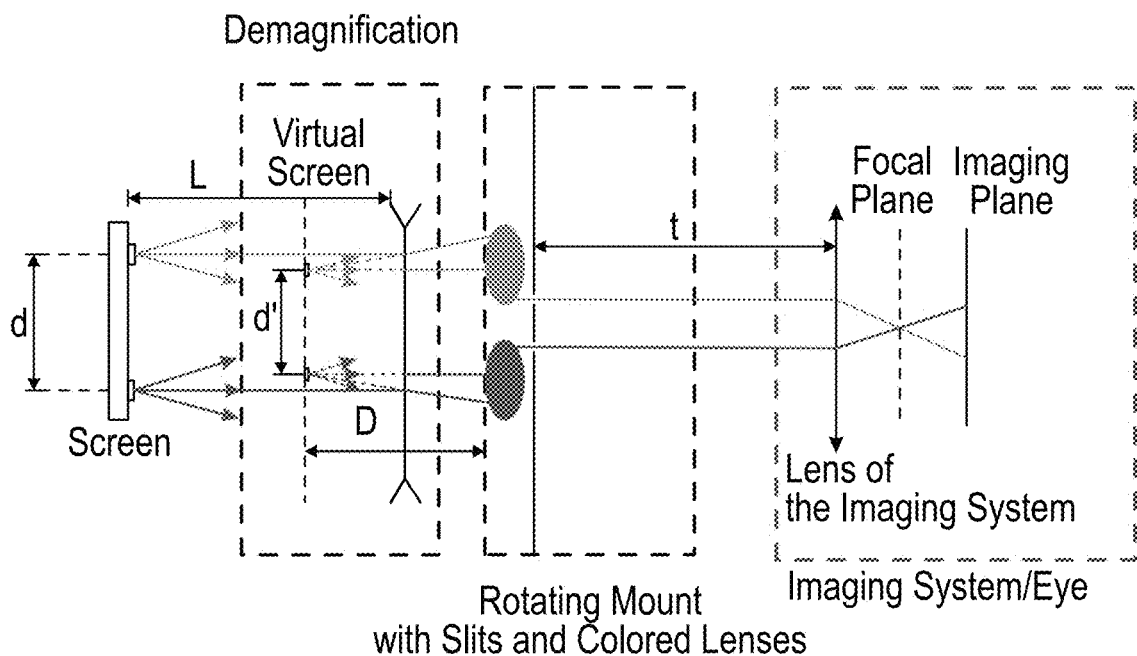
FIG. 14 depicts a second disclosed embodiment.

In another embodiment of this invention the complex lens and the demagnification stage can be replaced with a pair of colored lens and a slit for each lens mounted on a rotating mount, as shown in FIG. 14. The colored lens act as a filter to eliminate crosstalk. One lens can be colored red and the second one green. Thus, the light emitted from the green line cannot pass through the red colored lens and vice-versa. After each lens there is a slit that act as a shutter and increase the depth of field. Again, the usage of the slits doesn't reduce much the transmitted intensity. In this embodiment, there is no need of the magnification stage, since the exit pupil is determined solely by the distance between the two slits, and the crosstalk is eliminated by using colored lenses. In order to measure meridians at different angles the lens along with the slits are rotating using a rotating mount and follows the rotation on the screen. The rotation can happen either manually by the user or by using an electric motor. When the user proceed to the next meridian the application can automatically rotate the rotating mount.

Mechanical Tolerance Analysis.

If the whole system is translated parallel to the screen in a first order approximation, the error in the assessment of the refractive error would be minimal. The only effect it would have is that the user won't see the lines symmetrically around the center of its field of view and the intensity would be reduced. Next, every subsystem will be analyzed separately, focusing on the lateral displacement. The tilt tolerance can be easily calculated by converting the lateral tolerance into an angle (shown in the end of this section).

a. Demagnification

The demagnification is given by:

$$DM = \frac{h}{h'} = 1 + \frac{L}{f}$$

and the position of the virtual image and the size is respectively $$L' = \frac{fL}{L+f}, h' = \frac{fh}{L+f}$$

so a change of $\Delta L$ will induce a change in demagnification of $$\Delta DM = \frac{\Delta L}{f}$$

in the position of the virtual image of $$\Delta L' = \frac{f^2}{(L+f)^2}\Delta L = \frac{\Delta L}{DM^2}$$

and the size of the virtual image:

$$\Delta h' = -\frac{fh}{(L+f)^2}\Delta L = -\frac{h}{f}\frac{\Delta L}{DM^2}$$

The change in the size of the virtual image will directly induce a shift in the calibration, the change in the demagnification will directly affect the resolution of the system and the change in the position affects the performance of the following subsystems. The resolution is limited by c (pixel spacing) over DM so:

$$\Delta Resratio = -\frac{1}{DM^2}\Delta DM = -\frac{1}{f}\frac{\Delta L}{DM^2}$$

So if the demagnification factor is 3, the device is 9 times less sensitive. Hence in terms of tolerance it is beneficial to have high demagnification. It is even better to have long focal length. Therefore, it is preferable to achieve large magnification using longer length.

b. Parallel Beam Creation

If the optical source is not exactly on the focal point of the lenslet the beam after the lenslet will be either diverging or converging. Thus it will bias, shift our measurements. Thus our measurement of the power will be shifted by $$\Delta P = -\frac{1}{D^2}\Delta D$$

From this equation the change in the power due to the demagnification can be calculated as:

$$\Delta P_{demag} = -\frac{1}{(f_l + L')^2}\Delta(f_l + L') = -\frac{1}{(f_l + L')^2}\frac{\Delta L_d}{DM^2}$$

This change adds up with the bias due to change in demagnification and reduces the total effect.

c. Magnification Stage

This stage doesn't depend on the previous stage. It solely reduces the distance between two beams. If the distance between the two lenses is not correct, it will induce a bias in the refraction measurement. Again with a first order approximation is $$\Delta P = \frac{1}{L^2}\Delta L$$

The dominant factor is the lateral change of the demagnification stage and mainly the change in the distance of the two lines (2h'). This change in height induces a bias on the measured power. For low resolution the change in resolution due to the change in the demagnification is important especially for people with high refractive error. As an example, for a design with a demagnification factor equal to 3, and the distance between lines equal to 18 mm, and the distance of the concave lens from the screen equal to 30 mm.

Tilt can be converted into lateral displacement (at least in a first order approximation). Focusing only on the demagnification stage, which is the stage with the tightest tolerances, if the lens is tilted around the center, one side of lens comes closer to the screen and the other further away. Thus the net effect is zero. If the lens is tilted on the corner, only one side moves and the change in length is $\Delta L \approx 2h\Delta\theta$. The angle converts into a Power bias as follows:

$$\Delta P = -14.4\Delta\theta(\text{radians}) = -0.25\Delta\theta(\text{degrees})$$

Further Embodiments Include

Some current apparatuses and methods include lens-based refractometers that attach to a smartphone and work with a smart phone app that allows for accurate measurement of the optical system refractive error. In the case of the measured optical system being the human eye, an example of such a device is the Personal Vision Tracker (PVT) by EyeQue Corp (patent publication US20170215724A1 incorporated herein in its entirety as reference).

The PVT works by projecting an image of a defined geometrical pattern onto the user's retina, allowing the user to control an aspect of the properties of the image to achieve a well-defined goal, and then measuring a parameter of the image to deduce the required correction of the user optical system (e.g. their eye). As an example, the image could be on a screen of a smartphone to which an optical device is attached. Furthermore, an example of the image could be a set of parallel lines of different color (e.g. red and green). As the image is transmitted through the optical device the user adjusts the perceived distance between the lines on the screen to get them to a final position such as they appear in a well-defined relation, for example overlapping. The relation between the distance between the lines and the perceived overlap corresponds to the user's refractive error. An example of this implementation is shown in FIG. 15.

Figure 15:
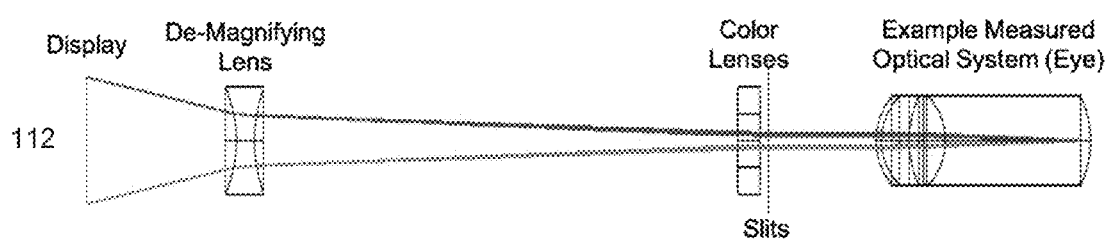
FIG. 15 depicts a disclosed embodiment

Referring to FIG. 15, this method and apparatus are limited in the measurement accuracy by the resolution of the phone. In today's smartphones the pixel density (resolution measured in pixels per inch, ppi) is around 326. There are phones that have higher resolutions (most common around 570 ppi) and phones with lower resolutions (down to below 250 ppi). The 326 ppi phones allow for accuracy in the order of 0.25 D within the scale of −10 D and +8 D. This accuracy level is adequate in most cases but might be a bit limiting (especially for lower resolution phones). Furthermore, this method requires an active display to control the distance between the lines.

As an alternative to this apparatus and method, the current invention proposes the following implementation of the refraction measurement. A display showing a geometrical image (for example to parallel lines, one green and one red) is presented to the user through an optical system (for example the system presented in FIG. 15). The user then controls the geometrical representation of the image through the measured optical system. In an embodiment of the invention, the control is done by modifying the distance of the display from the first lens. In another embodiment of the invention the control is done by modifying the focal length of the lens at the end of the device optical system, for example by using a variable focus lens, a zoom lens, or a liquid lens. The modification of the image by the user through the measured optical system is done to achieve a specific geometrical goal, for example overlapping of the lines. The system parameter (whether it is the distance offset, or the adjusted focal length of the lens is then recorded and correlated with the required optical correction of the measured system. An example of a measured system could be the user's eye. The correlation could be done for example by calibration, fitting to a curve/function, analytical or numeric calculation, by artificial intelligence, e.g. neural networks.

Figure 16:
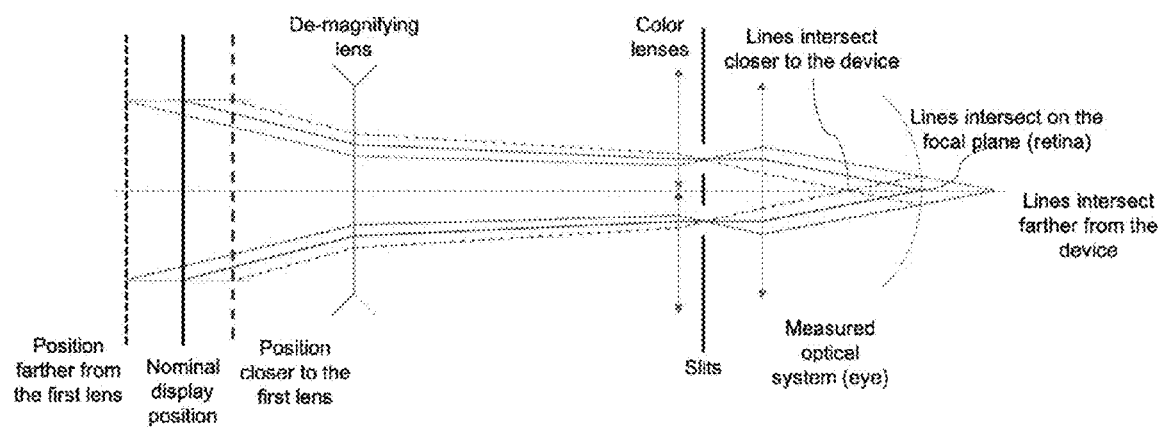
FIG. 16 depicts measurement concepts of a disclosed embodiment

Referring to FIG. 16, an explanation of a disclosed measurement principle is presented. At a nominal location of the display from the first lens of the device, the presented lines on the display appear to overlap on the focal plane of the measured optical system (e.g. the retina of the eye). As the display is translated away from the measured optical system, the lines appear to be getting farther away from each other in one direction, as the focal point (where the lines intersect) moves farther from the device. As the display is translated towards the first lens, the lines separate to the other direction and the focal point is shifted towards the device.

Figure 17:
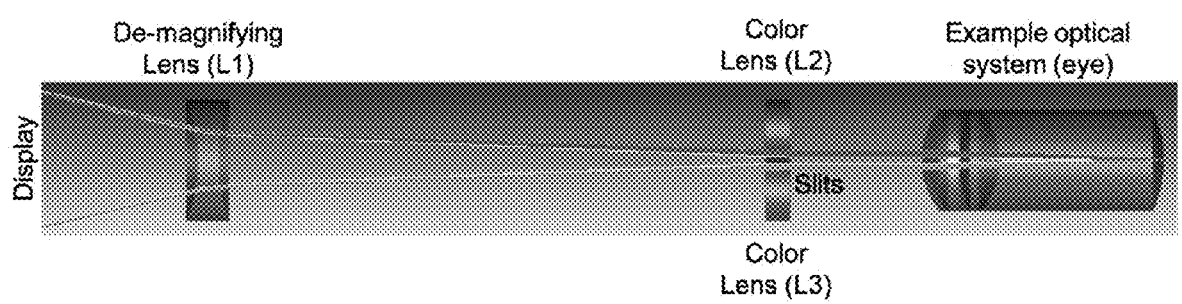
FIG. 17 depicts a disclosed embodiment based upon a linear translation mechanism for image modification
Figure 18:
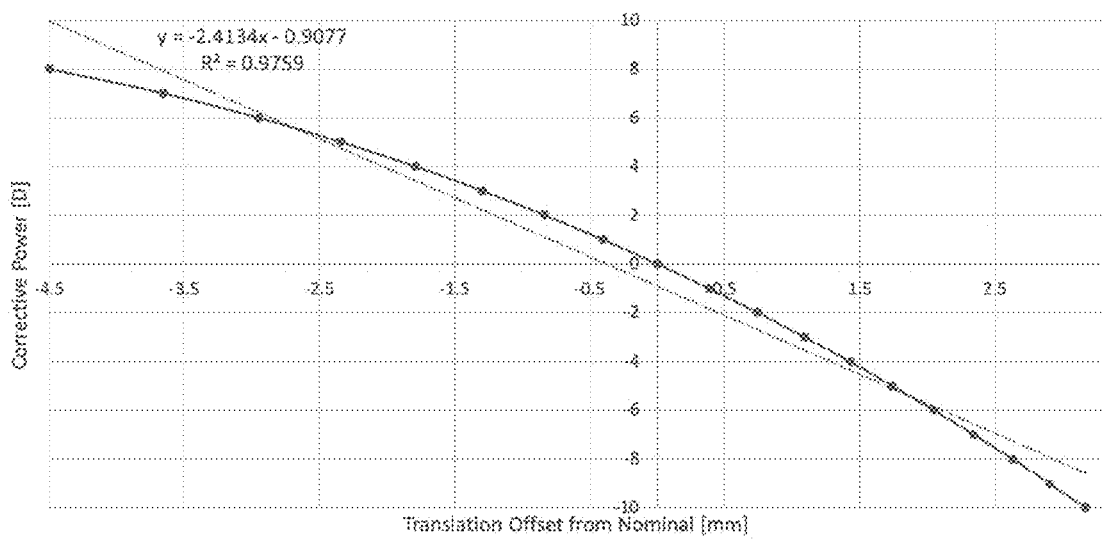
FIG. 18 depicts graph of corrective power [D] vs. Translation offset from Nominal [mm]

Referring to FIG. 17, an embodiment of the proposed invention based on the linear translation mechanism for the image modification is presented.

An optical refractor may comprise a demagnifier lens, L1, and two colored lenses, L2, green, and L3, Red. Adjacent to L2 and L3 are slits that allow passage of red and green light respectively. The resolution of the device can be determined by following the chief rays of the two lines at incremental distances of the screen from the first lens.

Referring to 18, a power-distance relation in a disclosed embodiment is shown. It should be noted that the dependency is not linear as to be expected. The slope of the curve determines the resolution. The expected average resolution in the presented case is approximately 2.5 D per mm (100 μm corresponds to about 0.25 D). The resolution of the device may be increased by changing the nominal distance between the lines or by increasing the focal length of the first lens as the angular sentence $\Psi$ of the two lines decrease. The resolution of the device is proportional to $1/\tan(\Psi)$.

Figure 19:
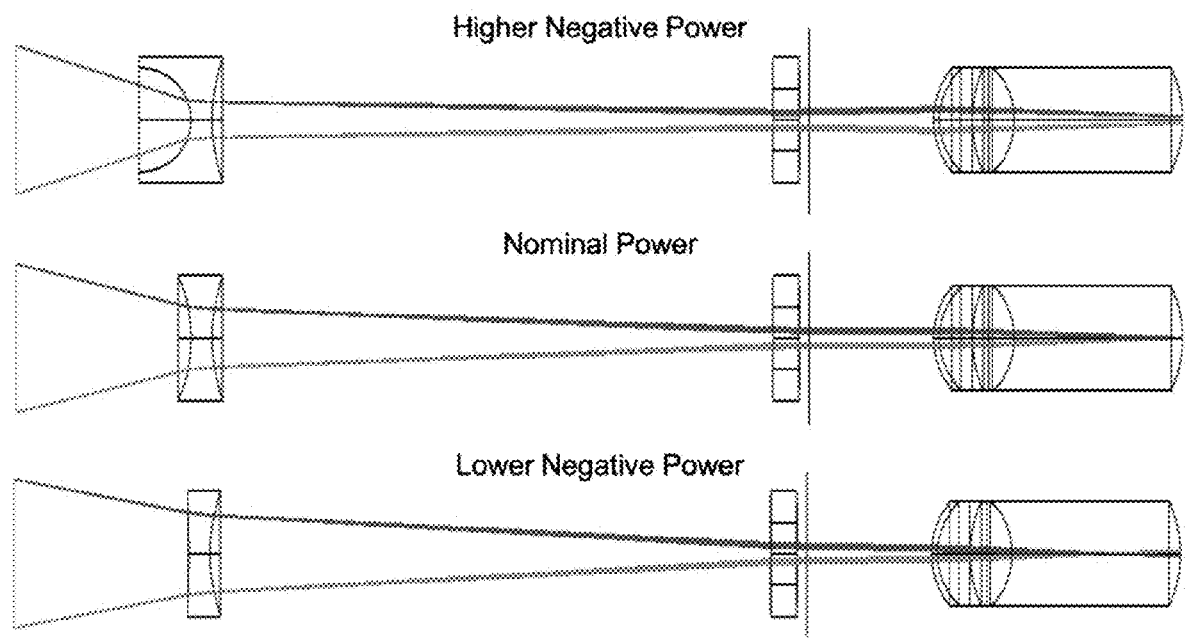
FIG. 19 depicts an alternative embodiment wherein a first lens is replaced with a variable focus lens

FIG. 19 presents an alternative embodiment of the invention where the first lens is replaced with a variable focus lens. In this embodiment, the focal length of the first lens is changed to achieve overlap between the lines on the display in the focal plane of the measured optical system (e.g. the retina for the human eye). FIG. 19 also shows the ray tracing of the nominal lens power as well as two other possible powers one, higher power (shorter absolute focal length, in the example case, more positive power) of the first lens will correspond to the focal point of the two lines intersecting to be farther from the device, while a lower power (longer absolute focal length, and in the example case, more negative power) corresponds to the lines intersecting closer to the device.

As the modification mechanism is independent of the actual distance between the lines the display could be of a multitude of options including for example: a screen (including a smartphone screen), an LED strip (including one where the lines are made of diffusers ad color filters), a semitransparent plaque with backlight, a light box illuminating a mask transmitting the desired pattern.

To get a measure of the astigmatic aspect of the measured optical system (e.g. the eye), the device can be rotated through different meridians and the resultant data of required corrective optical power can be used to compute the refractive error of the measured optical system in Focus (Sphere) and Astigmatism (Cylinder, and Axis).

Figure 20A:
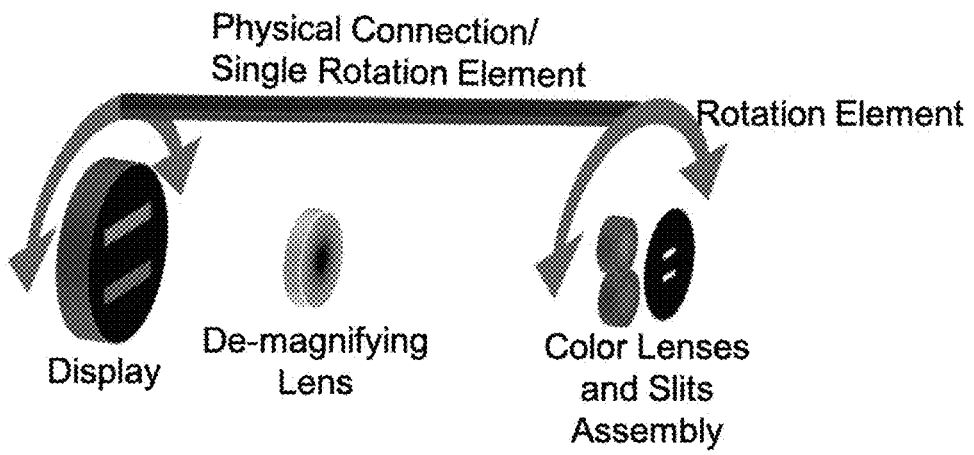
FIGS. 20A, 20B and 20C depict disclosed embodiments wherein a translational element moves a display along the optical axis
Figure 20B:
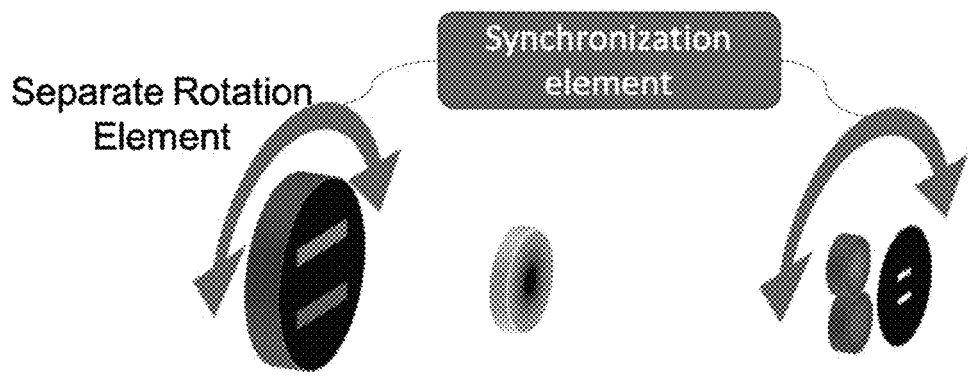
Figure 20C:
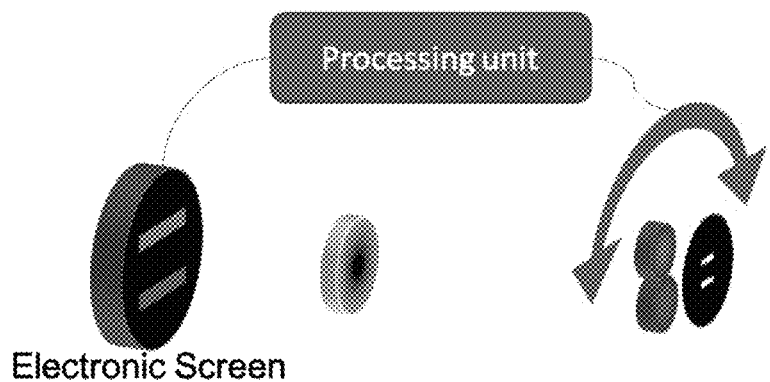

Referring to FIGS. 20A, 20B and 20C, alternatively, the display, color lenses and slits could be rotated in correspondence, instead of the entire device.

In an embodiment of the invention, a translational element moves a display along the optical axis, and a single rotational element allows the slits and color lenses on the eye piece and the display to rotate in tandem through different meridians (FIG. 20A). In another proposed embodiment of the invention the rotation is achieved by implementing two rotational elements, one on the display and another for the slits and color lenses (FIG. 20B). In this embodiment special care needs to be taken for the synchronization between the rotational elements. In yet another implementation of the invention, the rotation of the display is done by digital means, with the display being an electronic screen. In this case the rotation of the slits and color lenses is done by a rotational element (FIG. 20C).

Both linear translation elements and rotational elements could be of various manifestations including for example, fully manual control, completely automatic or electronic control and any combination thereof. The proposed embodiments could be implemented in either a monocular or binocular form. In an embodiment of the invention, the device would connect to a smart phone or other Bluetooth enabled computational device to transmit data to perform calculations and analysis on the computational device or enabling transmission of the data to a cloud to perform the calculations and analysis there. The connection may also be used for control of the different aspects of the device for example the rotation and translation of the corresponding elements.

The above detailed description of embodiments of the invention is not intended to be exhaustive or to limit the invention to the precise form disclosed above. While specific embodiments of, and examples for, the invention are described above for illustrative purposes, various equivalent modifications are possible within the scope of the invention, as those skilled in the relevant art will recognize. For example, while steps are presented in a given order, alternative embodiments may perform routines having steps in a different order. The teachings of the invention provided herein can be applied to other systems, not only the systems described herein. The various embodiments described herein can be combined to provide further embodiments. These and other changes can be made to the invention in light of the detailed description.

All the above references and U.S. patents and applications are incorporated herein by reference. Aspects of the invention can be modified, if necessary, to employ the systems, functions and concepts of the various patents and applications described above to provide yet further embodiments of the invention.

These and other changes can be made to the invention in light of the above detailed description. In general, the terms used in the following claims, should not be construed to limit the invention to the specific embodiments disclosed in the specification, unless the above detailed description explicitly defines such terms. Accordingly, the actual scope of the invention encompasses the disclosed embodiments and all equivalent ways of practicing or implementing the invention under the claims.

While certain aspects of the invention are presented below in certain claim forms, the inventors contemplate the various aspects of the invention in any number of claim forms.

The disclosed embodiments may include the following items:

1. A method to measure refraction errors in an optical system (300), using a first lens (200), a second lens and a display (112) the method comprising the steps of:
   disposing the second lens proximal to the optical system;
   disposing the first lens within sight lines of the second lens;
   disposing the display within sight lines of the first lens;
   changing the distance of the display from the first lens until an indicia upon the display is aligned as observed by the optical system;
   using the changed distance of the display to derive spherical error of the optical system.

2. The method of item 1 wherein the first lens comprises a demagnification lens.

3. The method of item 2 wherein the second lens comprises a first colored lens and a second colored lens.

4. The method of item 3 wherein the second lens defines two slits.

5. The method of item 4 wherein the indicia transmitted from the second lens to the optical system comprises first color and a second color.

6. The method of item 1 wherein the indicia upon the display comprises a first symbol and a second symbol.

7. The method of item 6, wherein the first and second symbols are respectively, vertical and horizontal colored lines.

8. The method of item 7, wherein the colored lines are red and green.

9. The method of item 1 wherein the display comprises one of the following selected from the group compressing (a screen ((including a smartphone screen)), an LED strip ((including one where the lines are made of diffusers and color filters)), a semitransparent plaque with backlight, a light box illuminating a mask transmitting the indicia.

10. The method of item 1 further including the step of rotating the second lens along an optical axis through different meridians and measuring the distance of movement of the second lens at each meridian in response to a changed projection upon the screen and using the measured distances of the second lens to derive further errors of refraction of the optical system.

11. The method of item 1 further including the step of rotating the display in synchronization to a rotation of the second lens along an optical axis through different meridians and measuring the distance of movement of the second lens at each meridian and using the measured distances of the second lens to derive further errors of refraction of the optical system.

12. A method to measure refraction errors in an optical system (300), using a first lens, a second lens and a display (112) the method comprising the steps of:
   disposing the second lens proximal to the optical system;
   disposing the first lens within sight lines of the second lens; wherein the first lens is a variable focus lens;
   disposing the display within sight lines of the first lens;
   changing the focal length of the first lens until an indicia upon the display is aligned as observed by the optical system;
   using the changed focal length of the first lens to derive spherical error of the optical system.

13. A system to measure refraction errors in an optical system (300), comprising a first lens, a second lens and a display the system comprising:
   the second lens disposed in a position proximal to the optical system;
   the first lens disposed within sight lines of the second lens;
   the display disposed within sight lines of the first lens;
   the display having an adjustable linkage from the first lens with the adjustable linkage having means to adjust in length until an indicia upon the display is aligned as observed by the optical system;
   the changed distance of the display functioning as a variable to derive spherical error of the optical system.

14. A system to measure refraction errors in an optical system (300), comprising a first lens, a second lens and a display (112) the system comprising:
   the second lens disposed proximal to the optical system;
   the first lens disposed within sight lines of the second lens;
   wherein the first lens is a variable focus lens;
   the display disposed within sight lines of the first lens;
   means to measure change in the focal length of the first lens used to aligned indicia upon the display as observed by the optical system;
   the changed distance of the focal length of the first lens used as a variable to derive spherical error of the optical system.

What is claimed is:

1. A method to measure refraction errors in an optical system, using a first lens, a second lens and a display the method comprising the steps of:

a. disposing the second lens proximal to the optical system;
b. disposing the first lens within sight lines of the second lens;
c. disposing the display within sight lines of the first lens;
d. changing the distance of the display from the first lens until an indicia upon the display is aligned as observed by the optical system;
e. using the changed distance of the display to derive spherical error of the optical system; and
f. the second lens comprises a first colored lens and a second colored lens.

2. The method of claim 1 wherein the first lens comprises a demagnification lens.

3. The method of claim 1 wherein the first colored lens defines two slits and and wherein the second colored lens defines two slits.

4. The method of claim 1 wherein the indicia transmitted from the second lens to the optical system comprises a first color and a second color.

5. The method of claim 1 wherein the indicia upon the display comprises a first symbol and a second symbol.

6. The method of claim 5, wherein the first and second symbols are respectively, vertical and horizontal colored lines.

7. The method of claim 6, wherein the colored lines are red and green.

8. The method of claim 1 wherein the display comprises one of the following selected from the group compressing a screen, an LED strip, a semitransparent plaque with backlight, a light box illuminating a mask transmitting the indicia.

9. The method of claim 1 further including the step of rotating the second lens along an optical axis through different meridians and measuring the distance of movement of the second lens at each meridian in response to a changed projection upon the screen and using the measured distances of the second lens to derive further errors of refraction of the optical system.

10. The method of claim 1 further including the step of rotating the display in synchronization to a rotation of the second lens along an optical axis through different meridians and measuring the distance of movement of the second lens at each meridian and using the measured distances of the second lens to derive further errors of refraction of the optical system.

11. A method to measure refraction errors in an optical system, using a first lens, a second lens and a display the method comprising the steps of:
a. disposing the second lens proximal to the optical system;
b. disposing the first lens within sight lines of the second lens; wherein the first lens is a variable focus lens;
c. disposing the display within sight lines of the first lens;
d. changing the focal length of the first lens until an indicia upon the display is aligned as observed by the optical system;
e. using the changed focal length of the first lens to derive spherical error of the optical system.

12. A system to measure refraction errors in an optical system, comprising a first lens, a second lens and a display the system comprising:
a. the second lens disposed in a position proximal to the optical system;
b. the first lens disposed within sight lines of the second lens;
c. the display disposed within sight lines of the first lens;
d. the display having an adjustable linkage from the first lens with the adjustable linkage having means to adjust in length until an indicia upon the display is aligned as observed by the optical system;
e. the changed distance of the display functioning as a variable to derive spherical error of the optical system.

13. A system to measure refraction errors in an optical system, comprising a first lens, a second lens and a display the system comprising:
a. the second lens disposed proximal to the optical system;
b. the first lens disposed within sight lines of the second lens; wherein the first lens is a variable focus lens;
c. the display disposed within sight lines of the first lens;
d. means to measure change in the focal length of the first lens used to aligned indicia upon the display as observed by the optical system;
e. the changed distance of the focal length of the first lens used as a variable to derive spherical error of the optical system.

* * * * *